(12) United States Patent
Wolfberg et al.

(10) Patent No.: US 8,892,181 B2
(45) Date of Patent: Nov. 18, 2014

(54) NON-INVASIVE FETAL MONITORING

(71) Applicants: Adam J. Wolfberg, Boston, MA (US); Jay Ward, Stratham, NH (US); James K. Robertson, Bradford, MA (US)

(72) Inventors: Adam J. Wolfberg, Boston, MA (US); Jay Ward, Stratham, NH (US); James K. Robertson, Bradford, MA (US)

(73) Assignee: MindChild Medical, Inc., North Andover, MA (US)

( * ) Notice: Subject to any disclaimer, the term of this patent is extended or adjusted under 35 U.S.C. 154(b) by 165 days.

(21) Appl. No.: 13/653,700

(22) Filed: Oct. 17, 2012

(65) Prior Publication Data
US 2013/0102857 A1    Apr. 25, 2013

Related U.S. Application Data

(60) Provisional application No. 61/550,024, filed on Oct. 21, 2011.

(51) Int. Cl.
| | | |
|---|---|---|
| *A61B 5/0444* | (2006.01) | |
| *A61B 5/0448* | (2006.01) | |
| *A61B 5/00* | (2006.01) | |
| *A61B 5/11* | (2006.01) | |

(52) U.S. Cl.
CPC .............. *A61B 5/0444* (2013.01); *A61B 5/743* (2013.01); *A61B 5/1116* (2013.01); *A61B 5/6804* (2013.01)
USPC ........................... 600/391; 600/393; 600/511

(58) Field of Classification Search
CPC .......................... A61B 5/0444; A61B 5/0448
USPC .................. 600/376, 391–393, 511
See application file for complete search history.

(56) References Cited

U.S. PATENT DOCUMENTS

| | | | |
|---|---|---|---|
| 3,703,168 | A | 11/1972 | Frink |
| 4,211,237 | A | 7/1980 | Nagel |
| 4,945,917 | A | 8/1990 | Akselrod et al. |
| 5,372,139 | A | 12/1994 | Holls et al. |
| 5,666,959 | A | 9/1997 | Deans et al. |
| 5,704,365 | A | 1/1998 | Albrecht et al. |
| 5,846,189 | A | 12/1998 | Pincus |
| 5,846,558 | A | 12/1998 | Nielsen et al. |
| 6,658,284 | B1 | 12/2003 | Rosen et al. |
| 6,751,498 | B1 | 6/2004 | Greenberg et al. |

(Continued)

FOREIGN PATENT DOCUMENTS

| | | |
|---|---|---|
| JP | 2005-503883 A | 2/2005 |
| JP | 2007-301358 A | 11/2007 |
| JP | 2009-160410 A | 7/2009 |
| JP | 2011-516238 A | 5/2011 |

OTHER PUBLICATIONS

Blumensath, et al., "Blind Separation of Maternal and Fetal ECG's using any Number of Channels", IDCOM & Joint Research Institute for Signal and Image Processing, Jan. 4, 2007, pp. 1-7.

(Continued)

*Primary Examiner* — Lee S Cohen
(74) *Attorney, Agent, or Firm* — Thomas C. Meyers; Brown Rudnick LLP

(57) ABSTRACT

A non-invasive fetal monitoring system includes a plurality of contact elements, each of the contact elements comprising a plurality of electrodes configured in a unique pattern. The plurality of contact elements are configured for attachment to an external skin surface of a pregnant female for detecting fetal and/or maternal electrical activity.

48 Claims, 10 Drawing Sheets

(56) References Cited

U.S. PATENT DOCUMENTS

| | | | |
|---|---|---|---|
| 6,785,569 | B2 | 8/2004 | Schmidt et al. |
| 7,333,850 | B2 | 2/2008 | Marossero et al. |
| 7,532,923 | B1 | 5/2009 | Hayes-Gill et al. |
| 7,616,980 | B2 | 11/2009 | Meyer |
| 7,860,557 | B2 * | 12/2010 | Istvan et al. ............ 600/509 |
| 7,925,323 | B2 | 4/2011 | Meyer |
| 7,949,389 | B2 | 5/2011 | Wolfberg et al. |
| 8,064,991 | B2 | 11/2011 | Hersh et al. |
| 8,244,941 | B2 | 8/2012 | Robertson et al. |
| 2004/0243015 | A1 | 12/2004 | Smith et al. |
| 2005/0267377 | A1 | 12/2005 | Marossero et al. |
| 2005/0277841 | A1 * | 12/2005 | Shennib .................. 600/511 |
| 2006/0149597 | A1 | 7/2006 | Powell et al. |
| 2006/0241510 | A1 | 10/2006 | Halperin et al. |
| 2007/0213627 | A1 | 9/2007 | James et al. |
| 2007/0260133 | A1 | 11/2007 | Meyer |
| 2007/0260151 | A1 | 11/2007 | Clifford |
| 2008/0125668 | A1 | 5/2008 | Graupe et al. |
| 2008/0183092 | A1 | 7/2008 | Smith et al. |
| 2009/0177101 | A1 | 7/2009 | Hersh et al. |
| 2009/0259133 | A1 | 10/2009 | Wolfberg et al. |
| 2010/0022865 | A1 | 1/2010 | Meyer |
| 2010/0137727 | A1 | 6/2010 | Sameni et al. |
| 2010/0191119 | A1 | 7/2010 | Muthya et al. |
| 2012/0016209 | A1 | 1/2012 | Wolfberg et al. |
| 2012/0083676 | A1 | 4/2012 | Wolfberg et al. |

OTHER PUBLICATIONS

Clifford G, Sameni R, Ward J, et al., "Clinically accurate fetal ECG parameters acquired from maternal abdominal sensors," Am J Obstet Gynecol 2011; 204:1.e1-1.e5.

Clifford, et al., "Comparing the Fetal ST Segment Acquired Using a Fetal Scalp Electrode and Abdominal Electrodes," Poster from 2010, 1 page.

Clifford, et al., "Model-based filtering, compression and classification of the ECG", Int. J. Bioelectromagnetism, vol. 21 (2) (2005), pp. 101-104.

Copel, et al., Oral Plenary Session I, General Abstracts 1-8, Am J Obstet Gynecol, Supplement to Jan. 2011, www.AJOG.org, 323 pages.

Ferrario, et al., "Comparison of Entropy-Based Regularity Estimators: Application to the Fetal Heart Rate Signal for the Identification of Fetal Distress," IEEE Transactions on Biomedical Engineering, vol. 53, No. 1, 2006, pp. 119-125.

Graatsma E, Jacob B, van Egmond L, Mulder E, Visser G., "Fetal electrocardiography: feasibility of long-term fetal heart rate recordings," BJOG 2009;116:334-338.

Graatsma, et al., "Maternal Body Mass Index Does Not Affect Performance of Fetal Electrocardiography," Thieme eJournals—Abstract, Amer J Perinatol 2010; 27(7): 573-577.

Li, et al., "Robust Heart Rate Estimation From Multiple Asynchronous Noisy Sources Using Signal Quality Indices and a Kalman Filter", Physiol. Meas., vol. 29, 2008, pp. 15-32.

McDonnell, et al. "Evaluation of the fetal T/R ratio using a fetal scalp electrode and abdominal sensors," Poster from 2011, 1 page.

McDonnell, et al., "Comparing the Fetal T/R ratio Using a fetal scalp electrode and Abdominal Sensors," Abstract from 2011, 1 page.

Mulder, Eduard J.H., et al., "Antenatal Transabdominal Fetal ECG for Heart Rate Monitoring: Quality Assessment of a Renewed Monitoring Technique," American Journal of Obstetrics & Gynecology—Abstract 628 (Dec. 2007) p. S181.

Noninvasive Observation of Natal Activity (NONA) (Poster) Garment Project, Apr. 3, 2008, 1 page.

Patent Cooperation Treaty, International Preliminary Report on Patentability, PCT/US2009/040624, date of issuance Oct. 19, 2010, 7 pages.

Patent Cooperation Treaty, Notification of Transmittal of International Search Report, PCT/US2009/040624, mailed Jun. 5, 2009, 3 pages.

Patent Cooperation Treaty, Written Opinion of the International Searching Authority, PCT/US2009/040624, mailed Jun. 5, 2009, 6 pages.

Reinhard, et al., "Comparison of non-invasive fetal electrocardiogram to Doppler cardiotocogram during the 1st stage of labor," J. Perinat. Med. 38 (2010), pp. 179-185.

Sameni, et al., "Accuracy of fetal heart rate acquired from sensors on the maternal abdomen compared to a fetal scalp electrode," Abstract from 2010, 1 page.

Sameni, et al., "Accuracy of Fetal Heart Rate Acquired from Sensors on the Maternal Abdomen Compared to a Fetal Scalp Electrode," Poster from 2010, 1 page.

Sameni, et al., "Accuracy of fetal heart rate acquired from sensors on the maternal abdomen compared to a fetal scalp electrode," Abstract from 2010, 2 pages.

Sameni, et al., "Electrode Selection for Noninvasive Fetal Electrocardiogram Extraction Using Mutual Information Criteria," Jul. 8-13, 2006, American Institute of Physics, vol. 872, pp. 97-104.

Sameni, et al., "Model-Based Bayesian Filtering of Cardiac Contaminants from Biomedical Recordings," Physiological Measurement 29, 5 (2008) 595-613; DOI: 10.1088/0967-3334/29/5/006.

Sameni, et al., "Multichannel ECG and Noise Modeling: Application to Maternal and Fetal ECG Signals", EURASIP Journal on Advances in Signal Processing, vol. 2007, Article ID 43407, 2006, 14 pages.

Sameni, et al., "Multichannel Electrocardiogram Decomposition Using Periodic Component Analysis," IEEE Transactions on Biomedical Engineering, vol. 55, No. 8, Aug. 2008, pp. 1935-1940.

Sameni, et al., "Noninvasive Extraction of Fetal Cardiac Signals from Maternal Abdominal Recordings," Sep. 14, 2008, pp. 1-20.

Sameni, Reza, "Extraction of Fetal Cardiac Signals from an Array of Maternal Abdominal Recordings," Presentation at Grenoble INPG, Grenoble, France, Jul. 7, 2008, 40 pages.

Sameni, Reza, et al., "Thesis: Extraction of Fetal Cardiac Signals from an Array of Maternal Abdominal Recordings," Institut Polytechnique de Grenoble & Sharif University of Technology (Jul. 2008) 109 pages.

Syed, et al, "A Framework for the Analysis of Acoustical Cardiac Signals", IEEE (2006), pp. 1-13.

Syed, et al., "Association of Morphologic Entropy in Fetal ECG with Inflammatory Cytokines and Markers of Neuronal Injury," Poster from 2010, 1 page.

Syed, et al., "Association of Morphologic Entropy in Fetal Electrocardiograms with Inflammatory Cytokines and Markers of Neuronal Injury," Abstract from 2010, 1 page.

Syed, Zeeshan, et al., "Clustering and Symbolic Analysis of Cardiovascular Signals: Discovery and Visualization of Medically Relevant Patterns in Long-Term Data Using Limited Prior Knowledge," EURASIP Journal on Advances in Signal Processing, vol. 2007, Article ID 67938 (2006), 16 pages.

Vrins, et al., "Abdominal Electrodes Analysis by Statistical Processing for Fetal Electrocardiogram Extraction." Proceedings of the Second International Conference, Feb. 16-18, 2004, pp. 244-249.

Vrins, et al., "Electrode Selection for Non-Invasive Fetal Electrocardiogram Extraction Using Mutual Information Criteria", e-mail: vrins@dice.ucl.ac.be, www.dice.ucl.ac.be/~vrins, 2 pages.

Wolfberg, Adam, et al., "Development of a Fetal ECG Device—MindChild Medical, Inc.," Device Conference Poster 2008, 1 page.

Wolfberg, et al., "A Comparison of Subjective and Mathematical Estimations of Fetal Heart Rate Variability", The Journal of Maternal-Fetal & Neonatal Medicine, Informa Healthcare http://www.informaworld.com/smpp/title~content=t713453317, 2008, 5 pages.

Wolfberg, et al., "Development of a computer-based algorithm to distinguish minimal from moderate fetal heart rate variability," Poster from Jan. 31, 2007, 1 page.

Wolfberg, et al., "Entropy of Fetal EKG Associated with Intrapartum Fever", Conference Abstract, Sep. 30-Oct. 2, 2007, 1 page.

Wolfberg, et al., "Entropy of Fetal EKG Associated with Intrapartum Fever," Poster from Jan. 28, 2008, 1 page.

Wolfberg, et al., "Entropy of fetal EKG associated with intrapartum fever," Sep. 2007, PowerPoint slides, 13 pages.

(56) References Cited

OTHER PUBLICATIONS

Wolfberg, et al., "Entropy of Fetal EKG Associated with Intrapartum Fever," SMFM Abstracts, 2007, 1 page.
Wolfberg, et al., "Validation of a computer algorithm that measures fetal heart rate variability," NE Perinatol Abstract, Jul. 12, 2006, 1 page.
Notification of Transmittal of the International Search Report and the Written Opinion for PCT/US2012/060552, mailed Mar. 4, 2013, 2 pages.
International Search Report for PCT/US2012/060552, mailed Mar. 4, 2013, 3 pages.
Written Opinion for PCT/US2012/060552, mailed Mar. 4, 2013, 5 pages.

\* cited by examiner

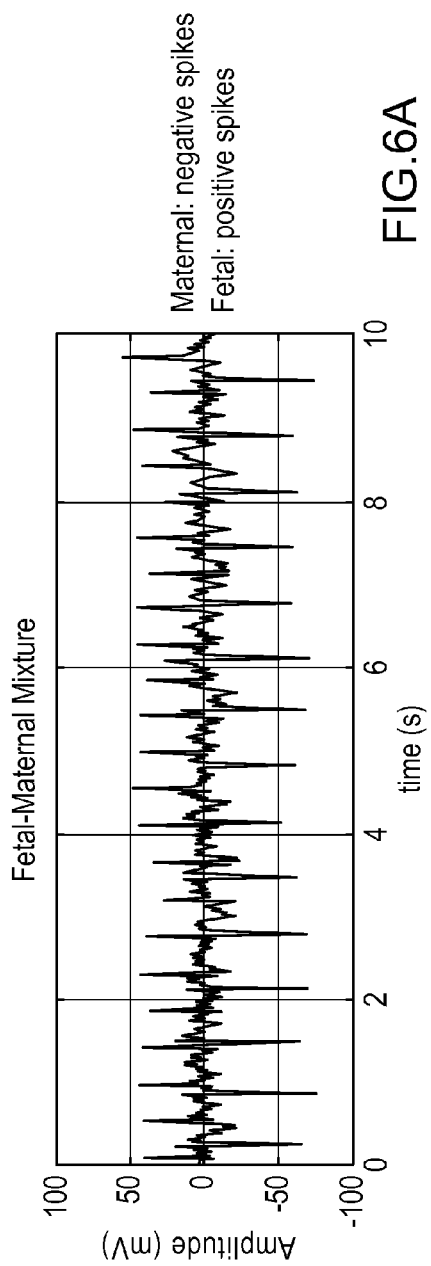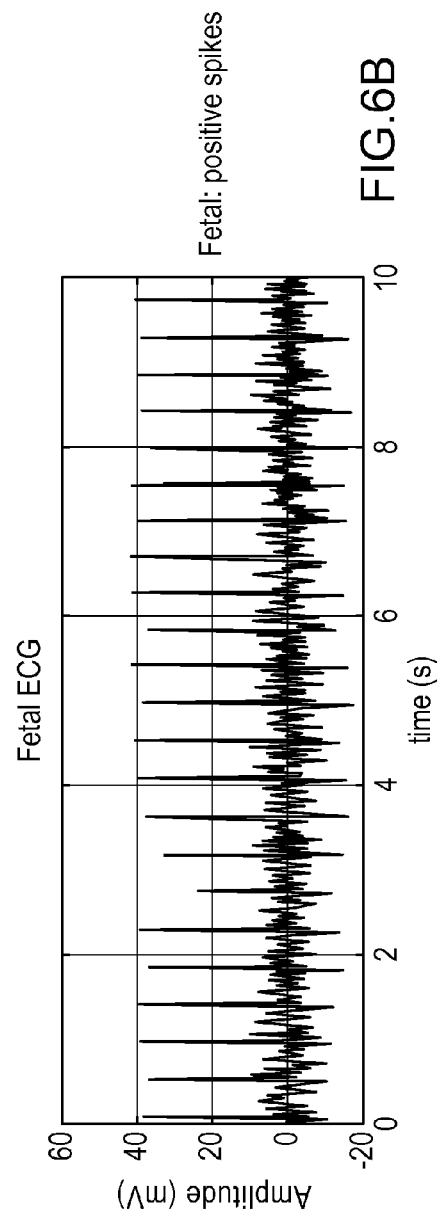

NON-INVASIVE FETAL MONITORING

TECHNICAL FIELD

The invention relates to non-invasive fetal electrocardiogram (fECG) monitoring.

BACKGROUND OF THE INFORMATION

Electrocardiogram (ECG) monitoring has been widely used on adult patients for detecting medical conditions, for example, abnormities associated with the heart. Signals representing a patient's cardiac activities can be collected through a set of skin surface electrodes distributed over the patient's body, for example, attached to the patient's chest and limbs.

Monitoring of fetal ECG can be difficult due to the co-existence of maternal and fetal signals in raw signals acquired from a patient, as well as the relatively low fetal signal level relative to the maternal signal and other noise sources. Some conventional approaches to collecting fetal ECG signals include placing a wire electrode onto the fetal scalp. Although the fetal scalp electrode may provide a relatively clean fetal signal, this procedure can only be performed under limited clinical circumstances (e.g., when a patient is in labor, has ruptured amniotic membranes, and has a dilated cervix) and thus may not be suitable for the vast majority of pregnant and laboring patients. The placement of the fetal scalp electrode may also present certain risks to fetal safety, as rare cases of fetal scalp abscess and newborn death have been reported.

SUMMARY OF THE INVENTION

The invention relates to a safe, non-invasive fetal monitoring system that can be comfortably worn before and during labor. The system can be designed for a single-use. The fetal monitoring system utilizes unique electrode patterns configured to detect fetal electrical activity regardless of the position of the fetus within the mother. One or more patterns indicative of fetal cardiac activity, fetal brain activity, fetal body position, or a combination thereof, can be extracted from the detected fetal electrical activity using the fetal monitoring system.

In one aspect, the invention involves a system for monitoring fetal electrical activity that comprises a plurality of contact elements configured for attachment to an external skin surface of the pregnant female. A plurality of electrodes are associated with each of the plurality of contact elements such that the plurality of electrodes contact the external skin surface when the contact element is attached to detect fetal electrical activity. Each of the plurality of electrodes associated with the plurality of contact elements are configured in a unique pattern.

In certain embodiments according to this aspect of the invention, the plurality of contact elements are patches configured for attachment to the external skin surface, for example, via an adhesive. The patch can be made of any flexible material capable of contouring to the human body, such as a fabric.

When two or more of the contact elements are attached to the external skin surface, the unique electrode patterns are capable of detecting fetal electrical activity regardless of the position of the fetus within the pregnant female. In certain embodiments, one or more of the unique electrode patterns associated with the plurality of contact elements patterns is a predetermined pattern.

The plurality of electrodes associated with a contact element can be all dry electrodes, all gel-adhesive electrodes, or a combination of dry and gel-adhesive electrodes. The types of electrodes between the plurality of contact elements can vary (e.g., some include all dry electrodes, some include all gel-adhesive electrodes, some include a combination of both, etc.).

In certain embodiments, one or more of the unique electrode patterns associated with of each of the contact elements are configured in relation to an anatomical reference point on a pregnant female. For example, the one or more of the unique electrode patterns can be configured in relation to the maternal heart, the belly button, the iliac arch, the spine, or a combination thereof.

Each of the plurality of contact elements is associated with at least three electrodes (dry or gel-adhesive, or a combination of both). In certain embodiments, there is a minimum of 6 electrodes combined between the plurality of contact elements. In certain embodiments, there is a maximum of 64 electrodes combined between the plurality of contact elements. In a particular embodiment, there are 32 electrodes between the plurality of contact elements.

In certain embodiments, the plurality of contact elements are each configured for attachment to an external skin surface in the torso region of the pregnant female. Preferably, the plurality of contact elements are each configured for attachment to a different area of the torso. For example, one or more contact elements are configured for attachment to the abdominal region, one or more contact elements are configured for attachment to the lumbar region, one or more contact elements are configured for attachment to the side regions of the torso, or any combination thereof.

One or more of the contact elements each can include a reference element to guide attachment of the contact element to the external skin surface of the torso of the pregnant female.

In a particular embodiment, the fetal monitoring system of the invention includes at least four contact elements, each of the contact elements in association with a plurality of electrodes configured in a unique pattern with respect to each other. A first one of the contact elements is configured for attachment to the external skin surface of an abdominal region of the torso of the pregnant female and a second one of the contact elements is configured for attachment to the external skin surface of a lumbar region of the torso of the pregnant female, a third one of the contact elements is configured for attachment to the external skin surface of a right side of the torso of the pregnant female, and a fourth one of the contact elements is configured for attachment to the external skin surface of a left side of the torso of the pregnant female.

In another particular embodiment, the fetal monitoring system of the invention includes at least four contact elements, each of the contact elements in association with a plurality of electrodes configured in a unique pattern with respect to each other. Two of the contact elements are configured for attachment to the external skin surface of an abdominal region of the torso of the pregnant female, a third one of the contact elements is configured for attachment to the external skin surface of on the left side of the torso and wraps around to the left lumbar region of the pregnant female, and a fourth one of the contact elements is configured for attachment to the external skin surface of a right side of the torso and wraps around to the right lumbar region of the pregnant female.

One or more of the plurality of contact elements can further include an electronic identification tag, such as a radio-frequency identification tag. One or more of the plurality of contact elements may be configured for short or long range wireless transmission of fetal electrical activity (e.g., via a blue-tooth chip).

These and other aspects of the invention are described in further detail in the figures, description, and claims that follow.

BRIEF DESCRIPTION OF DRAWINGS

FIG. 6A shows a waveform of fetal-maternal mixture; FIG. 6B shows a waveform of fetal ECG extracted from the fetal-maternal mixture of FIG. 6A.

DESCRIPTION

Figure 1:
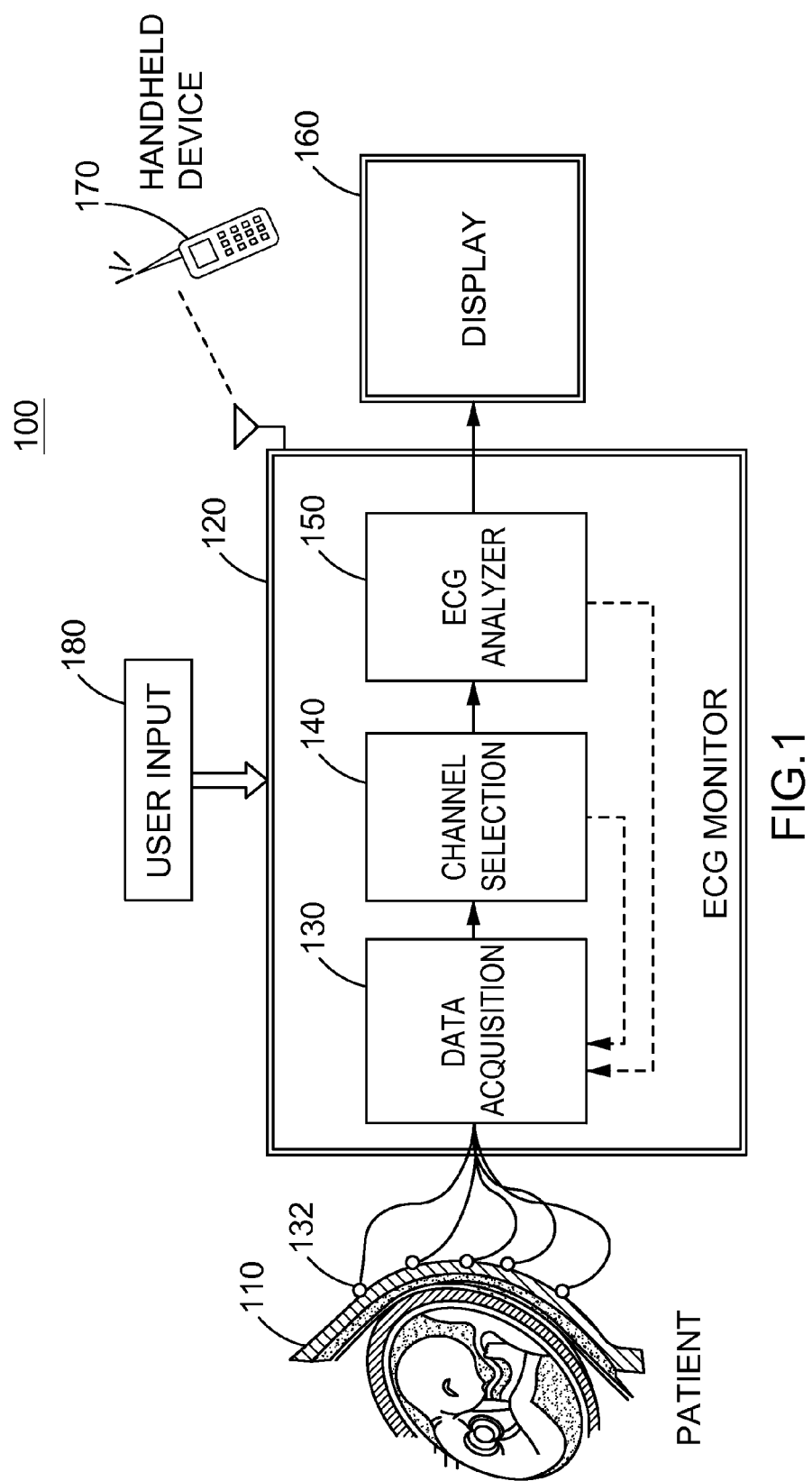
FIG. 1 is a block diagram of one embodiment of a fetal monitoring system.

Referring to FIG. 1, in some embodiments, a fetal monitoring system 100 is configured to identify characteristics of fetal ECG (fECG) signals collected from a patient 110 and based on these characteristics to detect events of clinical significance, including, for example, predicting impending fetal injury caused by inflammatory, hypoxic, or ischemic insults.

Very generally, the fetal monitoring system 100 includes an ECG monitor 120 that obtains and analyzes fetal ECG signals to generate data of clinical relevance. In some embodiments, the ECG monitor 120 makes use of morphological information in the fECG signal in addition to or instead of solely determining heart rate information. Data generated by the ECG monitor 120 can be presented to physicians in a variety of forms, for example, as printed on paper charts, shown on a display unit 160 (e.g., a computer screen), and transmitted via wireless signals to a handheld device 170 (e.g., a smart phone or PDA).

In this example, the ECG monitor 120 includes a data acquisition system 130, a channel selection module 140 (optional), and an ECG analyzer 150.

The data acquisition system 130 collects electrical signals, for example, electric potentials in the form of fetal-maternal mixtures, through a set of electrodes 132. These electrodes 132 include a set of electrodes distributed over the maternal abdomen, lower back, and/or sides, from which one or more leads are formed to generate electrical signals.

In this description, a lead is generally defined in association with a combination (e.g., a pair) of electrodes, which can be associated with an imaginary line in the body along which electrical signals are measured. A lead records the electrical signals produced by the heart (e.g., in the form of a voltage differential) from the corresponding combination of electrodes placed at specific points on the patient's body. Two different leads may use one or more common electrodes and therefore the number of leads in an ECG system is not necessarily in direct proportion to the number of electrodes placed on the patient's body. In some examples, the electrodes 132 are placed relatively far away from the maternal heart to reduce the influence of maternal signal in the fetal-maternal mixtures. In some other examples, the electrodes 132 may also include one or more electrodes placed on the maternal chest near the heart from which a maternal reference lead can be determined. The arrangement of the electrodes on the patient's body and the definition of lead pattern are selected depending on the particular implementation, as is discussed later is this document.

The signals collected by the data acquisition system 130 are transmitted to an ECG analyzer 150 that first digitizes raw ECG signals (e.g., at a sampling rate of 1,000 Hz and a resolution of 16 bits) for subsequent processing and analysis. In some examples, the raw signals are transmitted over multiple independent channels, for example, each channel for a different lead. In this example, a channel selection module 140 applies a channel selection algorithm that can discard certain channels of "weak" (low quality) signals to allow only "strong" (high quality) signals to be passed to the ECG analyzer 150. Some of the discarded channels contain primarily noise, for example, due to fetal position change or poor electrode conductivity (e.g., caused by the non-conductive gel used in an earlier ultrasound procedure). These channels are preferably rejected as the noise characteristics may not be amendable to the type of filtering technique designed for the system. Further discussion of the channel selection algorithm is provided in a later section.

Figure 2:
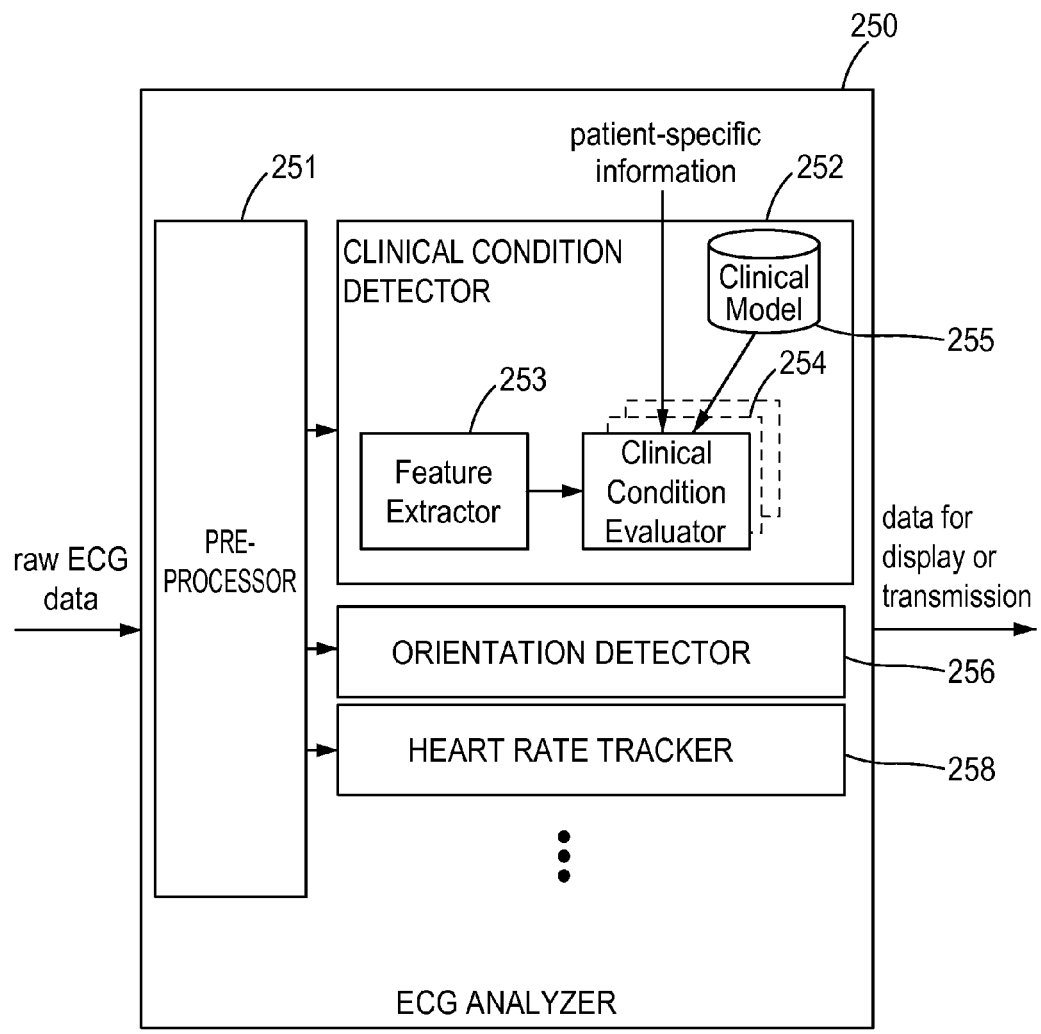
FIG. 2 is a block diagram of one embodiment of the ECG analyzer of FIG. 1.

Referring to FIG. 2, to obtain data of clinical significance from raw ECG signals, some embodiments of an ECG analyzer 250 include a pre-processor 251 that applies one or more filtering techniques (as will be discussed later) to generate processed ECG signals, for example, in the form of "clean" fetal ECG waveforms or metrics (i.e., parameters) of fetal-maternal ECG models. These processed signals are used by one or more analyzing modules, as described below.

One example of a type of an analyzing module is a clinical condition detector 252. Very generally, the clinical condition detector 252 includes a feature extractor 253 for extracting characteristics of the fetal and/or maternal ECG signals, such as heart rate variability, ECG morphology, and morphology classification and entropy, to assist clinical evaluation. For example, one or more morphological patterns in the fECG can be extracted, including but not limited to electrical activity amplitude, ST segment, QT interval, T/R ratio, R-peak, PR interval, or any combination thereof.

The extracted characteristics (e.g., morphological patterns in fECG), are then provided to a clinical condition evaluator 254, which identifies specific ECG patterns that are correlated with events of clinical significance using one or more clinical models 255 input in the clinical condition evaluator 254. The one or more clinical models 255 are configured to detect a biological condition in the pregnant mother based on fetal electrical activity, a biological condition in the fetus based on fetal electrical activity, a biological condition in the fetus based on maternal electrical activity, a biological condition in the pregnant mother based on maternal electrical activity, or any combination thereof.

The clinical condition evaluator 254 and/or clinical models 255 further include one or more electrophysiological patterns known to be associated with various medical conditions, as well as electrophysiological patterns associated with normal, healthy adults and/or fetuses (i.e., reference values). These known or standard electrophysiological characteristics are used by the one or more clinical models 255 to correlate electrophysiological behaviors (e.g., ECG patterns) of the fetus and/or the mother with statistical behaviors in large populations associated with medical conditions that may affect the health of the pregnant mother and/or the fetus during the pregnancy and/or labor. The resulting correlation is used to determine the susceptibility of the patient (mother and/or fetus) to such conditions.

An increase, a decrease or a substantial similarity between the electrophysiological characteristics extracted from the fetal electrical activity and/or the maternal electrical activity (e.g., morphological patterns such as electrical activity amplitude, ST segment, QT interval, T/R ratio, R-peak, PR interval), and one or more of the known/standard electrophysiological patterns, may be indicative of such conditions as described above, depending on the disorder or condition being evaluated. For example, a decrease in fetal electrical activity amplitude extracted from the detected fetal electrical activity as compared to a reference fetal electrical activity amplitude derived from a normal, healthy fetus may be indicative of fetal pericardial infusion, Rh incompatibility between the pregnant mother and the fetus, viral or parasitic infection in the pregnant female or the fetus, or Mirror syndrome in the pregnant female. As another example, an increase in the QT interval extracted from fetal electrical activity as compared to a reference QT interval derived from a normal, healthy fetus may be indicative of prescription drug abuse (e.g., selective serotonin re-uptake inhibitor) by the pregnant female.

For example, a data acquisition system 130 including a plurality of electrodes, such as the system shown in FIG. 10 and described below, is used to detect fetal electrical activity. One or more morphological patterns are derived from the detected fetal electrical activity using feature extractor 253. Clinical condition evaluator 254 then runs one or more clinical models 255 configured to detect a condition in the pregnant mother based on the morphological patterns extracted from the fetal electrical activity. Such clinical models 255 may be configured to detect one or more of chorioamnionitis, autoimmune disease (e.g., lupus or Sjogrens syndrome), inflammatory disease, maternal infection (bacterial, viral or parasitic infection such as Syphilis, Rubella, CMV parovirus, or toxoplasmosis), substance abuse, Rh incompatability with the fetus, Mirror syndrome, preeclampsia, and intrapartum fever.

One or more morphological patterns derived from the detected fetal electrical activity using feature extractor 253 can also be used in one or more clinical models 255 configured to detect a condition in the fetus, such as fetal hypoxia, fetal hypoxemia, fetal metabolic acidosis, fetal cardiac arrhythmia, fetal neuronal injury, fetal pericardial effusion, fetal heart block, fetal infection (bacterial, viral or parasitic infection such as Syphilis, Rubella, CMV parovirus, or toxoplasmosis, or sepsis), Rh incompatibility with the mother, and hydrops fetalis.

One or more of the clinical models 255 may also be configured to detect and correlate a fetal condition based on fetal electrical activity, with a separate condition that affects the mother, and vice versa. For example, fetal heart block has been associated with lupus or Sjogrens syndrome in the pregnant mother. As such, the clinical condition evaluator may include a clinical model 255 configured to detect fetal heart block based on fetal electrical activity, and to further detect lupus or Sjogrens syndrome in the pregnant female when fetal heart block is present.

Depending on the particular implementation, the clinical condition evaluator 254 may have separate modules (e.g., a chorioamnionitis evaluator, an intrapartum fever evaluator), with each module providing a measure of a degree of the presence of a particular aspect of fetal and/or maternal distress. Physicians may receive the outputs of the individual modules in confidence scores, for example, presented on a scale of 0 to 10 with "0" indicating no (or least) distress and "10" indicating the highest level of distress. The individual scores can also be combined to form an evaluation of overall fetal distress level indicating the general health condition of the fetus.

In some embodiments, the clinical condition evaluator 254 performs an automated diagnosis to identify medical conditions (e.g., using expert systems and/or human intervention) and/or to provide recommendation for follow-up procedures. In some examples, other clinical data (such as pathologic evaluations of serum samples from the umbilical cord) are collected from the patient in pregnancy or during labor and are used by the clinical condition evaluator 254 in conjunction with the identified ECG characteristics to help further determine the likelihood of impending fetal/neonatal injuries (such as brain injuries, cerebral palsy, and death).

Using the feature extractor 253, high quality fetal ECG data can be obtained from the patient under a variety of clinical conditions (e.g., pregnant or in-labor). The characteristics of the ECG data can be well preserved to enable clinical analysis that is otherwise unavailable using conventional techniques. Implementations of the feature extractor 253 and examples of clinical condition evaluator 254 are described in greater detail at a later section.

A second example of an analyzing module is a fetal orientation detector 256 that provides an estimate of fetal position within the mother.

Figure 3A:
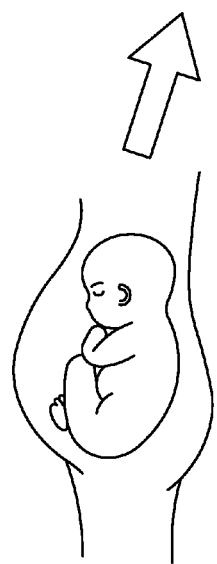
FIGS. 3A-3C illustrate fetal position changes during pregnancy.
Figure 3B:
Figure 3C:
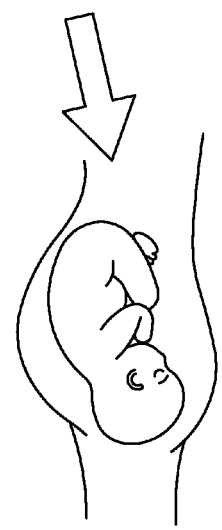

Referring to FIGS. 3A-3C, fetal position may change during various stages of pregnancy and the pre-labor position can affect the way by which the mother will deliver and whether certain cautionary steps need to be taken. In some applications, it is desirable to generate an estimate of fetal position as an output of the monitoring system, for example, providing a clinician with a continuous output.

In some examples, such a position estimate is determined as part of a multiple dipole modeling approach for extracting the fECG signal from the raw signals that include both fetal and maternal signals, in which estimated orientation of the dipole of the fetal heart provides an estimate of the orientation of the fetus relative to the mother's body.

In some examples, the fetal position is used as part of the feature extraction procedure, or as part of the clinical evaluation procedure. For example, signal acquisition in certain fetal positions may result in characteristically distinct signals, for example, that exhibit higher signal-to-noise characteristics. In some examples, automated clinical determinations are made as a function of the fetal position, for example, being performed only in certain fetal positions. An example of such a fetal position is a fetus with its back to the maternal abdominal wall, which may result in particularly high quality signals due to the short distance between the fetal heart and the surface electrodes. In some examples, the estimated fetal position is used to select electrodes in the channel selection module 140. In some examples, the estimated fetal position is used to determine signal and/or model characteristics related to various electrodes, for example, to determine signal transmission characteristics between the signal source (e.g., fetal heart) and the electrodes.

Other examples of analyzing modules implemented in the ECG analyzer 250 include a heart rate tracker 258, a fetal ECG waveform extractor (not shown), and possibly other modules that associate user-determined statistics with clinical analysis. The heart rate tracker 258 may provide a continuous output of fetal heart beat over time and automatically identify the occurrence of heart rate acceleration, deceleration, and certain types of irregularity that can be early manifestation of serious medical conditions such as cardiac arrhythmia.

Note that the pre-processor 250 may provide signals to various analyzing modules in different forms. In other words, the input data to the clinical condition detector 252 is not necessarily the same data provided to the orientation detector 256 or the heart rate tracker 258. Depending on the particular implementation, some analyzing modules may accept data representing "clean" fetal ECG waveforms, whereas others may accept data representing metrics of predefined fetal-maternal ECG models.

Figure 4:
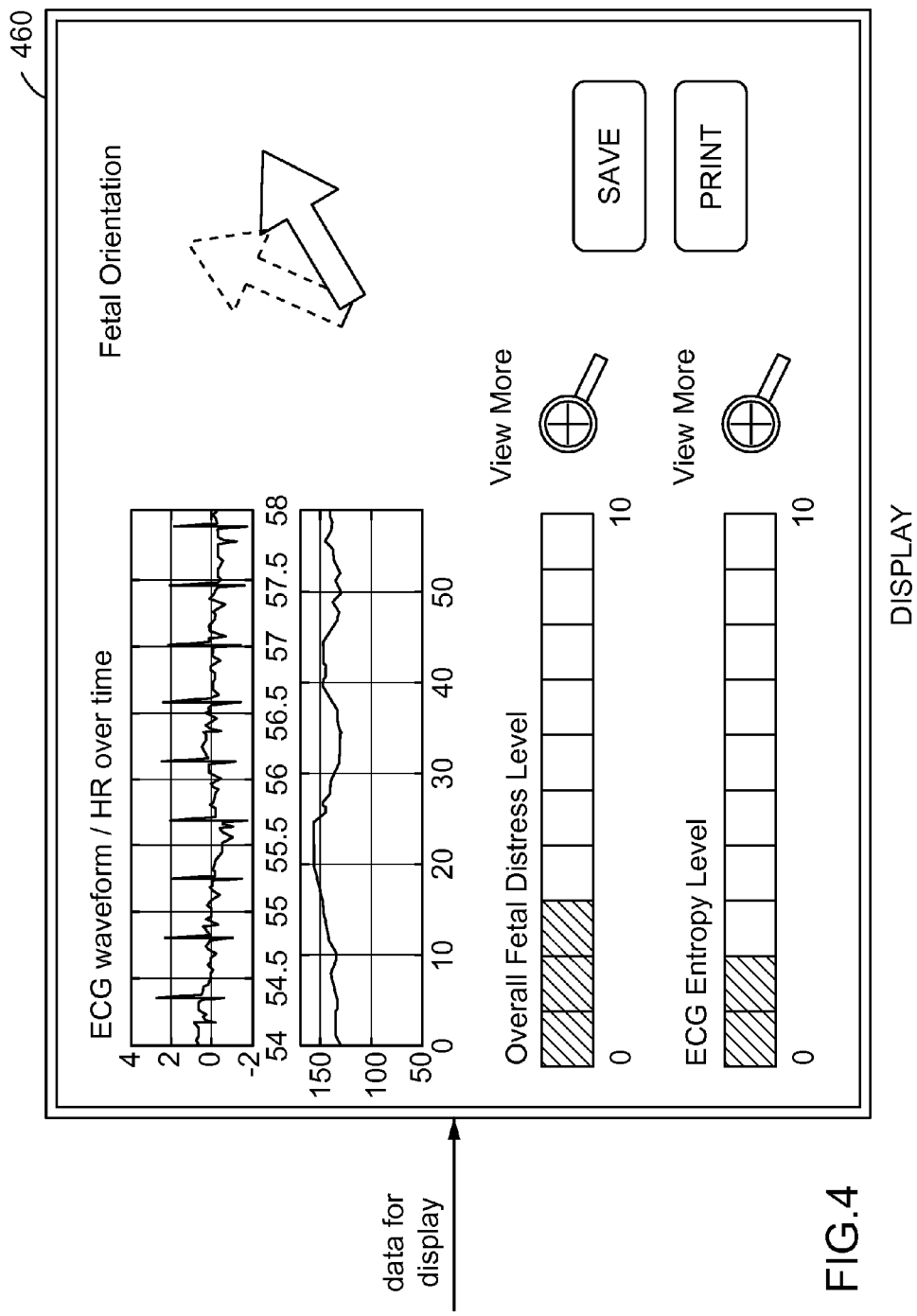
FIG. 4 shows an example of data display of the fetal monitoring system of FIG. 1.

FIG. 4 shows one example of a data display by which the outputs of various analyzing modules are presented to physicians, for example, on a computer screen or a handheld device. This display includes multiple regions that respectively show, for example, a fetal ECG waveform along with observed fetal heart rate, a fetal orientation pointer, an overall fetal distress index, an entropy index, and possibly other indices. In some examples, changes in fetal position since the most recent examination (or over the entire course of pregnancy) are also presented, for example, by loading prior position data from a patient database. In some examples, each index has a predefined "alert" level (e.g., a score of 6 out of 10) beyond which special attention (e.g., follow-up procedures) is indicated. In some examples, the monitoring system 100 also allows physicians to view detailed data, for example, the statistics upon which a particular index value is determined, when there is a need.

Depending on the particular implementation, ECG signals can be collected using non-invasive approaches with the electrodes 132 placed in a variety of arrangements. The following description provides two examples of electrode configurations suitable for use with the monitoring system 100 of FIG. 1.

Figure 5:
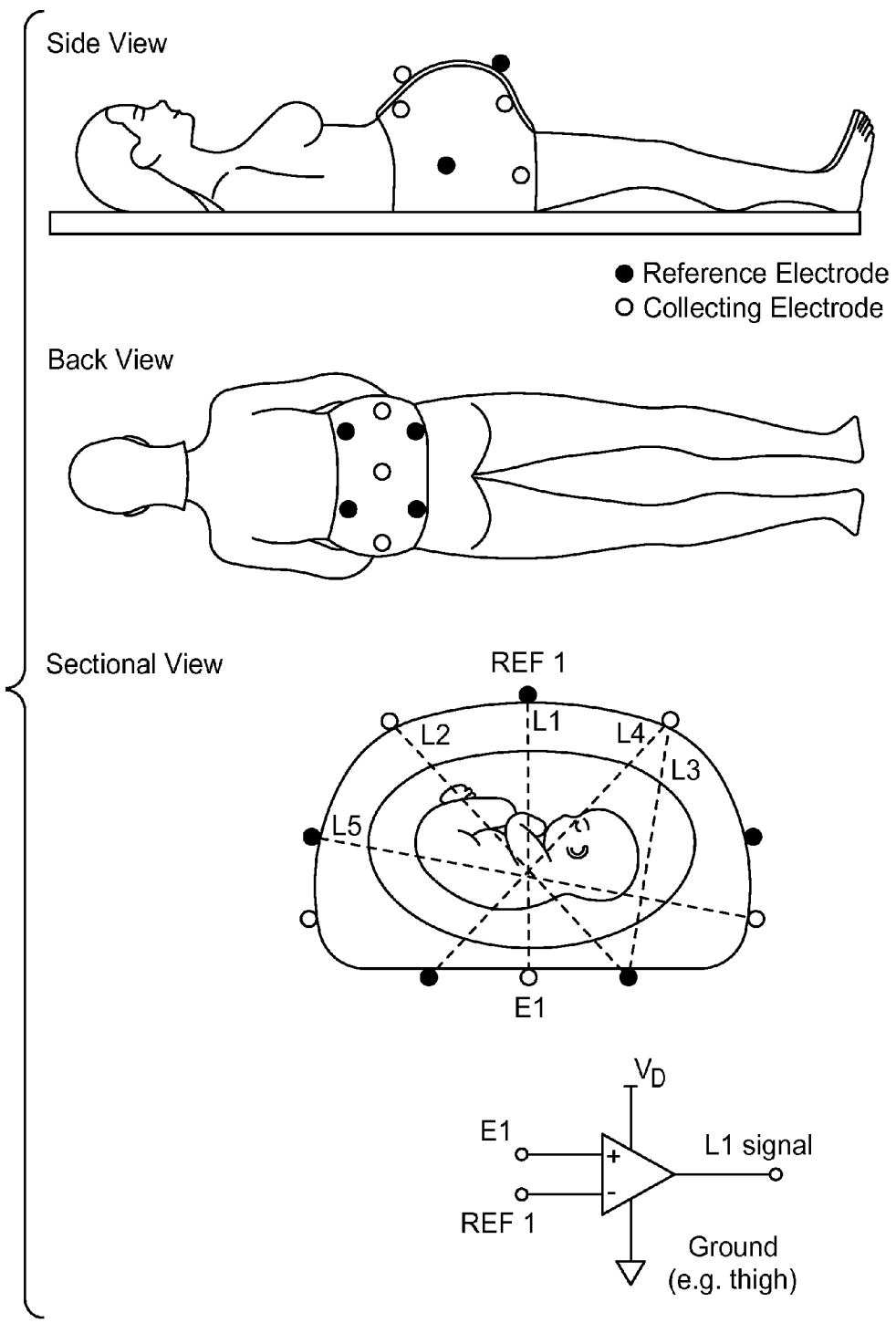
FIG. 5 shows an exemplary embodiment of a data acquisition system including a plurality of electrodes patterned on an wearable garment for use with the fetal monitoring system of the present invention.

Referring to FIG. 5, a second electrode configuration of some embodiments of the data acquisition system 130 is shown. Here, a set of dry electrodes (e.g., 132) are mounted on a convenient elastic monitoring garment that is strapped around the maternal abdomen to allow the electrodes to be distributed in a predetermined arrangement over the abdomen, the back, and on the sides of the patient. No fetal scalp electrode is necessary with this configuration. This configuration provides a non-invasive means to monitor fECG signals yet still capable of providing a sufficient set of useful fECG signals regardless of the fetal status.

In some embodiments, the electrode arrangement and the lead pattern by which electrical signals are collected can use conventional standards developed on adult patients. One example of such a conventional standard makes use of a well-established 12-lead pattern, with each lead recording the electrical activity of the adult heart from a different perspective. The signal of each lead can correlate with a different anatomical area of the heart, for example, to help identify acute coronary ischemia or injury. Fetal ECG signals are contained in some or all of the lead signals and may be extracted using various data extraction and filtering methods (as will be described later). In some cases, the isolation of fetal signals from fetal-maternal mixtures can be difficult as the conventional standards were developed based on adult models without accounting for the influence of fetal presence and the resulting fetal-maternal mixtures can be either poorly characterized or contain very low fetal components relative to the predominant maternal signals.

In some other embodiments, the electrode arrangement and the lead pattern use a design that suits the particular need of fetal ECG monitoring. FIG. 5 illustrates the placement of some electrodes in a side view, a back view, and a sectional view of the patient body. In this example, the entire set of electrodes forms at least of a group of cross-body leads each of which generates electrical signals along an imaginary line across the body, for example, from back to front, or from left side to right side. Some of these leads are each formed by a respective pair of electrodes, one being referred to as a collecting/positive electrode (e.g., E1) and the other being referred to as a reference/negative electrode (e.g., R1). The corresponding lead signal (e.g., L1) is obtained, for example, using a biomedical instrumentation amplifier that forms an amplified signal representing a voltage differential between the collecting electrode and the reference electrode. For some of these leads, the reference electrode is placed at the opposite side of the body to which the collecting electrode is attached. For example, some of the collecting electrodes are placed in the abdominal region while the corresponding reference electrode(s) are placed in the lumbar region. Similarly, some of the collecting electrodes can be placed in the left side of the body while the corresponding reference electrode(s) are placed in the right side of the body.

Using such a lead pattern, some of the collected signals can exhibit a stronger fetal component and/or contain less noise compared with lead signals collected using conventional adult standards. Depending on the particular implementation, each lead does not necessarily use a different electrode. In other words, some leads may be formed using collecting electrodes at various positions in the abdominal region against a single reference electrode in the lumbar region. In some examples, the reference electrodes and the collecting electrodes can be electrodes of different characteristics (for example, made from different materials, having different sixes, and/or exhibiting different levels of signal sensitivity) and be attached to the body using different attachment mechanisms (e.g., dry vs. wet). In some examples the set of electrodes is coupled to a lead reconfiguration module that can dynamically adjust electrode pairing, lead selection, and/or garment positioning based on feedback signals provided by the ECG analyzer 150 to account for, for example, fetal position changes, loss of electrode contact, and other events that may cause abrupt changes in certain electrode or lead signals.

Figure 10:
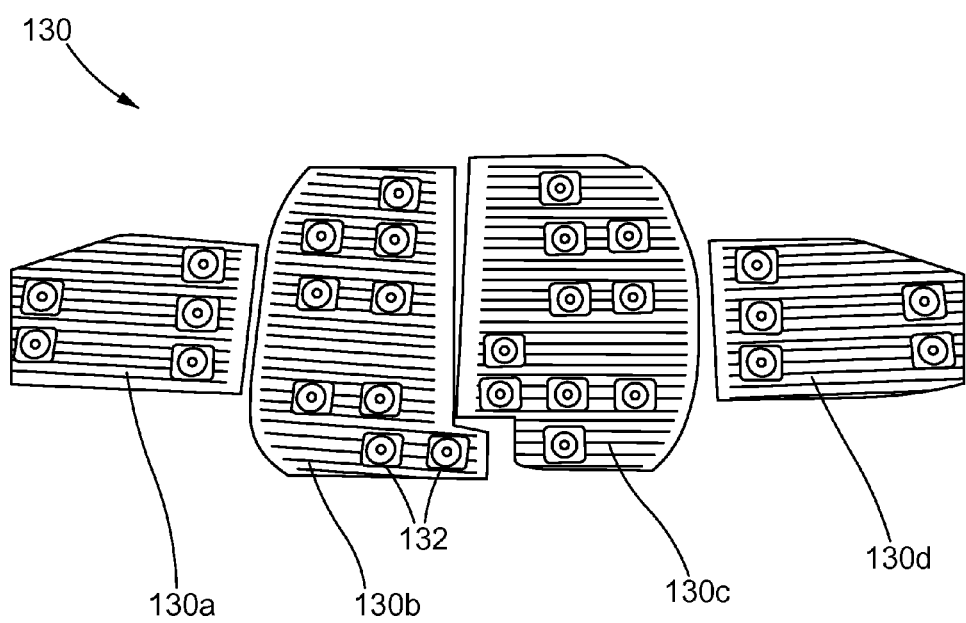
FIG. 10 shows an example of a data acquisition system including four contact elements, each contact element including a plurality of electrodes configured in a unique pattern.

An alternative configuration of a non-invasive data acquisition system 130 is shown in FIG. 10. This configuration provides a disposable, non-invasive means to monitor fECG signals that is capable of providing a sufficient set of useful fECG signals regardless of the fetal position. Here, a plurality of individual contact elements are provided (130*a*, 130*b*, 130*c*, 130*d*), each of the contact elements in association with a plurality of electrodes (e.g., 132). At least one side of each contact element is configured for attaching to an external skin surface. For example, an adhesive may be included on at least a portion of one side of each of the contact elements to facilitate attachment of the contact element to an external skin surface, forming an adhesive patch.

In the embodiment shown in FIG. 10, there are four contact elements shown, each of the contact elements associated with a plurality of electrodes configured in a unique pattern. However, the embodiment is not limited to the use of four contact elements. Any number of contact elements can be utilized. Preferably, two or more of the contact elements are used to detect fetal electrical activity by application of the contact element to an external skin surface. The detected fetal electrical activity is used to derive fetal cardiac activity, fetal brain activity, fetal body position, or any combination thereof, using the methods as previously described and as described in further detail below.

The electrodes are mounted on, or integrated into a supportive surface in a configuration that allows the electrodes to contact the external skin surface when the contact elements are attached to the external skin surface. The supportive surface can be any flexible material capable of contouring to the human body, and is preferably a fabric material that is configured for attaching to an external skin surface, as previously described.

The plurality of electrodes associated with each contact element can be dry electrodes, gel-adhesive electrodes or a combination of both dry and gel-adhesive electrodes. For example, each of the plurality of contact elements includes dry electrodes, or gel-adhesive electrodes. Alternatively, one or more of the plurality of contact elements includes dry electrodes, while one or more of the contact elements includes gel-adhesive electrodes. In some embodiments, one or more of the plurality of contact elements includes a combination of dry and gel-adhesive electrodes.

The plurality of contact elements can be of similar size and shape, or can vary in size and shape. In a particular embodiment, two or more of the plurality of contact elements are sized and shaped for attachment to different skin surface areas within the torso region a pregnant woman. For example, one or more contact elements can be sized and shaped for attachment to the maternal abdominal region, one or more contact elements can be sized and shaped for attachment to the maternal lumbar region, one or more contact elements can be sized and shaped for attachment to a side of the torso region of a pregnant woman (right side, left side, or both), one or more contact elements can be sized and shaped for attachment to the side region of the torso and the lumbar region, etc.

In one embodiment, at least one contact element is attached to the external skin surface to detect fetal electrical activity, the contact element being sized and shaped for attachment to the maternal abdominal region, the maternal lumbar region, a side of the torso region (right side or left side), or a side region and lumbar region of the pregnant woman (right side or left side). In another embodiment, at least two contact elements are attached to the external skin surface and used in conjunction to detect fetal electrical activity, both contact elements being sized and shaped for attachment to the maternal lumbar region. In yet another embodiment, at least two contact elements are attached to the external skin surface and used in conjunction to detect fetal electrical activity, where at least one of the contact elements is sized and shaped for attachment to the maternal abdominal region, and at least one other contact element is sized and shaped for attachment to the maternal lumbar region, a side of the torso region, or a side region and lumbar region of the pregnant woman (right side or left side). In still another embodiment, at least three contact elements are attached to the external skin surface and used in conjunction to detect fetal electrical activity, where at least one of the contact elements is sized and shaped for attachment to the maternal abdominal region, at least one of the contact elements is sized and shaped for attachment to the maternal lumbar region, and at least one of the contact elements is sized and shaped for attachment to a side of the torso region of a pregnant woman (right side or left side). In yet another embodiment, four contact elements can be used in conjunction to detect fetal electrical activity, where one of the contact elements is sized and shaped for attachment to the maternal abdominal region, one of the contact elements is sized and shaped for attachment to the maternal lumbar region, and two of the contact elements are sized and shaped for attachment to the sides of the torso region of a pregnant woman. Alternatively, four contact elements can be used in conjunction to detect fetal electrical activity, where two of the contact elements are sized and shaped for attachment to the maternal abdominal region, and two of the contact elements are sized and shaped for attachment to the side regions and lumbar regions of the torso or a pregnant woman (FIG. 10).

One or more of the contact elements can include a reference element to guide attachment of the contact element to a particular external skin surface area on the body of a pregnant woman. In a particular embodiment, one or more of the contact elements includes a reference element to guide attachment of the contact element to a particular external skin surface area within the torso region of a pregnant female. The reference element can be a marker, included in or on the contact element. For example, the marker can be one or more written notations on the supportive surface of the contact element, one or more colored indicators associated with the contact element, or one or directional indicators in or on the contact element. Alternatively, the reference element can be one or more of the plurality of electrodes themselves.

The plurality of electrodes associated with the plurality of contact elements configured in a unique pattern relative to the each other. The unique electrode patterns among the plurality of contact elements are preferably predetermined patterns which facilitate the detection of fetal electrical activity regardless of the position of the fetus within the pregnant female.

A minimum number of electrodes is required on each contact element in order to detect fetal electrical activity, and can vary, depending on the number of contact elements used in conjunction on the external skin surface of pregnant female in order to detect fetal electrical activity. In some embodiments, each of the unique electrode patterns of plurality of contact elements includes at least three electrodes (dry, gel-adhesive or both). In certain embodiments, there are a minimum of six electrodes combined between the plurality of contact elements. In other certain embodiments, there are a maximum of sixty-four electrodes combined between the plurality of contact elements. In a particular embodiment, there are a total of thirty-two electrodes combined between the plurality of contact elements.

One or more of the contact elements are attached to one or more locations along front, back and/or sides of the torso region of a pregnant woman to distribute the predetermined electrode arrangements on/around the maternal abdominal region, as previously described. Similar to the elastic garment configuration described above, the collective electrodes between the plurality of contact elements forms one or more groups of cross-body leads when applied to the external skin surface, each of which generates electrical signals along an imaginary line across the body, for example, from back to front, or from left side to right side. Some of these leads are each formed by respective pairs of collecting/positive electrodes (e.g., E1) and reference/negative electrodes (e.g., R1)). The corresponding lead signal (e.g., L1) can be obtained using a biomedical instrumentation amplifier that forms an amplified signal representing a voltage differential between the collecting electrode and the reference electrode. In some embodiments, a reference electrode is associated with a contact element that is attached at the opposite side of the body to which a collecting electrode associated with another contact element is attached. For example, a contact element including one or more of the collecting electrodes is attached to an external skin surface in the abdominal region while a contact element including one or more corresponding reference electrode(s) is attached to an external skin surface in the lumbar region. Similarly, a contact element including one or more of the collecting electrodes can be attached to an external skin surface on the left side of the body while a contact element including one or more corresponding reference electrode(s) are placed on the right side of the body.

The predetermined pattern of electrodes on one or more of the contact elements can be configured in relation to an anatomical reference point, such as the maternal heart, the belly button, the iliac arch or the spine of the pregnant woman. For example, the plurality of electrodes associated with a contact element sized and shaped for attachment to an external skin surface in the maternal abdominal region may be configured in a predetermined pattern in relation to the maternal heart, the belly button, or the iliac arch of the pregnant woman, or any combination thereof. In another example, the plurality of electrodes associated with a contact element sized and shaped for attachment to an external skin surface in the maternal lumbar region may be configured in a predetermined pattern in relation to the maternal heart, the spine, the iliac arch of the pregnant woman, or any combination thereof. In still another example, the plurality of electrodes associated with a contact element sized and shaped for attachment to an external skin surface on a side of the torso region of a pregnant woman may be configured in a predetermined pattern in relation to the iliac arch, the maternal heart, or the spine of the pregnant woman, or both.

One or more of the contact elements can include an electronic identification tag, such as a radio-frequency identification tag. One or more of the contact elements can also be configured for short or long-range, wireless transmission of the detected fetal electrical activity (e.g., via a blue-tooth chip).

The data acquisition system comprising a plurality of contact elements, as described herein, provides several advantages over the elastic monitoring garment configuration previously described. For example, by utilizing a plurality of contact elements, the data acquisition system is better adapted for use on pregnant women of various sizes and shapes, allowing for more accurate placement of the electrodes. The direct application to the skin (e.g., via adhesives) provides improved electrode contact, and therefore improved signal efficiency, regardless of movement by the pregnant woman. As such, the use of a plurality of contact elements allows for improved comfort of the pregnant woman before and during labor. Additionally, the single-use nature of the contact elements avoids any complications associated with prior use of the electrodes, or stretching of the elastic garment.

In the exemplary electrode configurations shown in FIGS. 5 and 12, one reason to record a large number of abdominal and back signals described above is that the fetal ECG tends to manifest in only a subset of these leads, yet the actual combination is dependent on the state of the fetus, the time through pregnancy, the degree of electrical contact, and the location and orientation of the fetus or fetuses. Therefore, the channel selection module 140 is configured to adaptively select channels of "strong" (high quality) signals and discards channels of "weak" signals. As some of the abdominal signals will contain primarily noise, preferably, these channels are discarded from processing.

One technique used by the channel selection unit 140 to select channels of useful signals is based on fusing multiple signal quality indices (SQI) derived from multiple ECG leads. In some examples, physiological SQIs are obtained by analyzing the statistical characteristics of each channel and their relationships to each other. For instance, by computing spectral coherence, statistical departures from Gaussianity, and the performance of differently-sensitive event detectors, this technique allows the automatic location of channels that contain useful signal, and discarding of those that contain primarily noise. Furthermore, a sliding scale of quality is available to enable the selection of different channels for different applications. Further discussion of this technique is provided by Li et al., in "Robust Heart Rate Estimation from Multiple Asynchronous Noisy Sources Using Signal Quality Indices and a Kalman Filter," published in Physiological Measurement 29 (2008) 15-32, the disclosure of which is incorporated herein by reference.

Some techniques to extract waveforms of fetal ECG signals from the fetal-maternal mixtures include signal processing and filtering techniques such as adaptive filtering (AF), nonlinear projective filtering (NLPF), neural networks, independent component analysis (ICA) and joint time-frequency analysis (JTFA). One limitation of these techniques lies in their dependencies on the signal-to-noise ratio (SNR) of the data and sensitivity to the frequent artifacts that manifest during fECG acquisition. Each technique may either perform an "in-band" filtering (removing frequency signals that are present in the fetal signal) or produce a phase distortion in the signal that has an unknown affect on the fECG morphology. These issues may result in significant changes in the clinical parameters one wishes to extract from the fECG.

Another issue in fetal ECG recording and analysis deals with signal distortions that result from the transmission of the fetal signal trough the mother's abdomen. To reach the surface electrodes, fECG signals pass through multiple layers of media (e.g., the vernix caseosa) each of which may have very different electric properties and some may cause significant attenuation the fetal ECG signals collected from surface electrodes. Since the effective frequency range of the ECG is below 1-2 KHz and considering the distance between the body surface electrodes and the cardiac sources, the propagation medium of the maternal body may be considered as a linear instantaneous medium. The body surface recordings are hence a linear instantaneous projection of the cardiac sources and artifacts onto the axes of the recording electrode pairs. It is however known that the electrical impedance of the body volume conductor changes with respiration. Therefore despite its linearity, the propagation medium is time-varying and the body surface recordings are rather non-stationary.

One method to address the issue of fetal ECG distortion due to transmission through media of varying dielectric constants is to use a model of the fetal cardiac source to constrain the filtering and feature extraction process. One technique, for example, applies a three-dimensional dynamic model to represent the electrical activity of the heart. More specifically, this model is based on a single dipole model of the heart and is later related to the body surface potentials through a linear model which accounts for the temporal movements and rotations of the cardiac dipole, together with a realistic ECG noise model. Details of this technique are further described by Sameni et al., in "Multichannel ECG and Noise Modeling: Application to Maternal and Fetal ECG Signals," published in EURASIP Journal on Advances in Signal Processing, Volume 2007, Article ID 43407, the disclosure of which is incorporated herein by reference.

FIG. 6A illustrates a typical mixture of maternal and fetal ECG. The maternal beats appear as negative spikes (HR=90 bpm), and the fetal beats appear as the smaller, positive spikes (HR=138 bpm). Both the fetal and maternal peak heights appear to be modulated by some low-frequency component (including, e.g., respiration). A fetus will "practice" respiration prior to birth, and this can lead to changes in intrathoracic pressure.

FIG. 6B illustrates the same signal after maternal subtraction using a model-based Kalman Filter tracking method described above. Note that the respiratory-modulation of the R-peaks and other features of the fECG are preserved in the waveform. These subtle features are essential in performing accurate feature analysis, such as R-peak location (e.g., for heart rate variability evaluation of sepsis), ST-elevation analysis (e.g., for ischemia) and QT interval analysis (for pro-arrhythmic indications).

Using these "clean" fetal ECG waveforms, the feature extractor 253 of FIG. 2 is able to identify characteristics of the waveforms that are associated with clinically relevant activities. Examples of ECG characteristics include heart rate variability, ECG morphology, and entropy. For instance, fECG signals may be grouped into different morphological classes, and each class may be further divided based on subtle morphological characteristics, based on which patterns of clinical relevance may be identified. Techniques of feature extraction are described in greater detail below in the following sections.

In some examples, the feature extractor 253 does not need the "clean" fetal ECG waveforms in order to obtain features of interest. For instance, the pre-processor 251 may process the raw ECG data to obtain metrics of ECG models or symbolization of ECG classification, based on which the feature extractor 150 may extract interesting features.

Heart rate variability (HRV) can be an important quantitative marker of cardiovascular regulation by the autonomic nervous system. Heart rate is generated by the intrinsic rhythm of the sinoatrial node in the heart, but constant input from the brainstem through a feedback loop in the autonomic nervous system closely modulates this rate. At rest, variation in heart rate arises predominantly from vagal tone governed by the vagus nerve nuclei. However, this variation is affected by the interaction between vagal and sympathetic activity, as well as by central respiratory and motor centers and peripheral oscillations in blood pressure and respiration.

In many clinical settings, evaluation of HRV is based on the subjective interpretation of this variable by clinicians using paper printouts that plot the fetal heart rate as a function of time. In some embodiments, heart beat may be detected by cross-correlating the cardiac signal with a reference heart beat trace from data recorded using the fetal ECG. The height of the cross-correlation peak (if it is not normalized) provides a measure of the strength of the signal and its similarity to the reference. The position of the peak provided an accurate measure of the exact time the beat occurred. These measures provided a way to reject signal that is not a fetal beat as well as to measure accurately the time between beats (the fetal heart rate). This approach provides data that can be used for analyses based on rate and HRV.

The cross-correlation can be used to locate fetal heart beats in the data, which can then be "windowed" out into a series of individual heart beats. The data is then subjected to a multivariate statistical analysis, and the results are used to group beats according to variations in the ensemble of heart beats. These data can be later used for the analysis of waveform morphology.

Fetal heart rate can be derived, as described above, using one of the data acquisition systems 130 described herein, to detect fetal electrical activity. The derived fetal heart rate can be compared to a known/standard heart rate of a normal, healthy fetus of comparable gestational age to determine whether the fetus is in distress. For example, a diminished fetal heart rate as compared to the known/standard heart rate is indicative of diminished fetal breathing movements, which in turn may be indicative of fetal hypoxia, placental failure, maternal or fetal ischemia, maternal or fetal infection, or other fetal distress.

The derived fetal heart rate can be used alone, or in combination with one or more morphological patterns extracted from the fetal electrical activity in the clinical condition evaluator 254 described above to detect a condition in the fetus and/or mother. The clinical condition evaluator 254 can include a clinical model 255 configured to detect diminished fetal heart rate, and to further detect diminished fetal breathing movements, fetal hypoxia, placental failure, maternal or fetal ischemia, and/or maternal or fetal infection when diminished fetal heart rate is present.

In some embodiments, the feature extractor 253 performs morphological analysis on the fECG signal. One approach to analyzing fetal ECG morphology uses clustering and symbolic analysis of ECG signals to discover medically relevant patterns. Very generally, ECG signals are classified into groupings that are morphologically similar according to a signal waveform similarity measure. In some examples, successive segments of the fECG waveform are formed with one segment per beat, and min-max clustering is then used to form the groupings according to pair-wise distance between the waveform segments. In some embodiments, the pair-wise distance between segments uses a dynamic time-warping (DTW) measure. In other examples, each segment is modeled using a parametric model (e.g., using a sum of displaced Gaussian components) and the distance between segments is based on a distance between the model parameters of the segments. The characteristics of the identified groups are used to determine a measure of morphological variation. In some examples, the segments of the fECG are labeled, for example, with discrete labels from an alphabet of symbols (e.g., 5 arbitrary labels). Then a statistical measure is determined from the sequence of labels, for example, in a sliding window of the signal.

One measure of morphological variation is an entropy of a sample distribution of the labels. In some examples, the entropy of a finite state model of the sequence is used. In some examples, the segments are not necessarily deterministically labeled (relying on a probability measure for beats in each hidden class), and the entropy of a underlying (e.g., hidden) sequence of segment classes is computed, thereby avoiding a need to first determine an accurate series of class labels, which may require a "clean" estimate of the fECG signal. Some aspects of these approaches are described by Syed et al., in "Clustering and Symbolic Analysis of Cardiovascular Signals: Discovery and Visualization of Medically Relevant Patterns in Long-Term Data Using Limited Prior Knowledge," published in EURASIP Journal on Advances in Signal Processing, Volume 2007, Article ID 67938, the disclosure of which is incorporated herein by reference.

Unlike the techniques incorporated into ECG monitors and ICU monitoring devices that compare observed phenomena to standardized patterns representing pathophysiological conditions (ventricular tachycardia or ST-depression, for example), some entropy-based approaches of the types described above do not necessarily assume a priori information about the ECG morphology. Each morphological class is represented by a symbol, and various patterns of symbols in sequence may have clinical significance. This analytic approach is suited for the fetal ECG data collected in the present system 100, because with the exception of ST-segment analysis, there are no formal systems for fetal ECG evaluation. Independence from a priori information can be useful in fetal applications where the information may not be available, or may be highly variable based on factors such as fetal age.

In some examples, model-based filtering is applied to the fECG signal, for example, prior to entropy-based analysis. For example, Gaussian based modeling as described in Clifford et al., "Model-based filtering, compression and classification of ECG," International Journal of Bioelectromagnetism Vol. 7, No. 1, pp 158-161, 2005, and in U.S. Patent Publication 2007/0260151, "Method and Device for Filtering, Segmenting, Compressing and Classifying Oscillatory Signals," published Nov. 8, 2007, are used in processing the fECG signals. These references are incorporated herein by reference. In some examples, the classification based on these techniques is used in determining entropy measures as described in the Syed reference. For example, each class may be characterized by a range of model parameters for that class (e.g., by partitioning the space of parameters values) or each class be associated with a distribution of the model parameters for that class.

In some embodiments, characteristics of ECG patterns are associated with events of clinical activity. Some examples of such clinical applications includes using an entropy measure of a fECG signal as an indicator of an inflammation condition, or as an indicator of a cause of an inflammation condition, for example, an infection-based cause of inflammation.

In an experimental application of signal processing and analysis techniques described above, the fECG waveforms of 30 recordings discovered a change in the morphology of the heart beat that occurs prior to the development of chorioamnionitis.

Figures 7A, 7B, 7C:
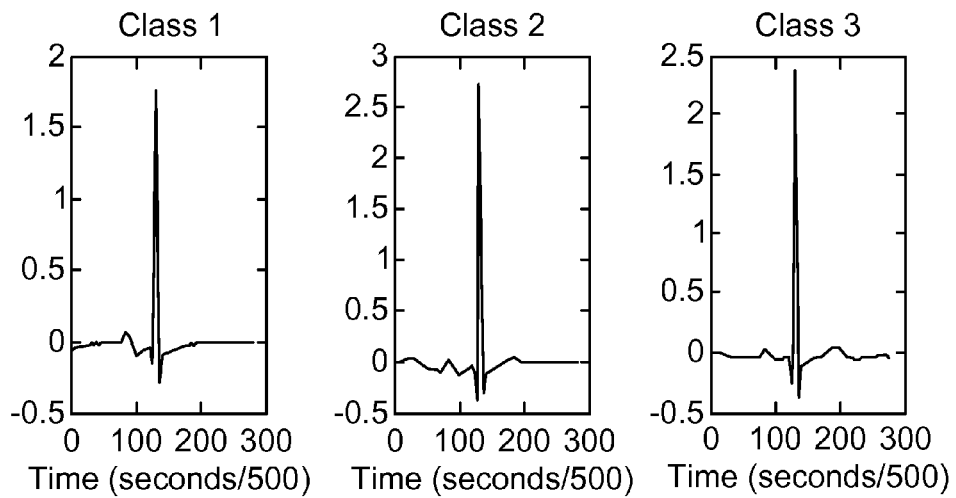
FIGS. 7A-7C show three exemplary classes of ECG waveforms, respectively.
Figure 7D:
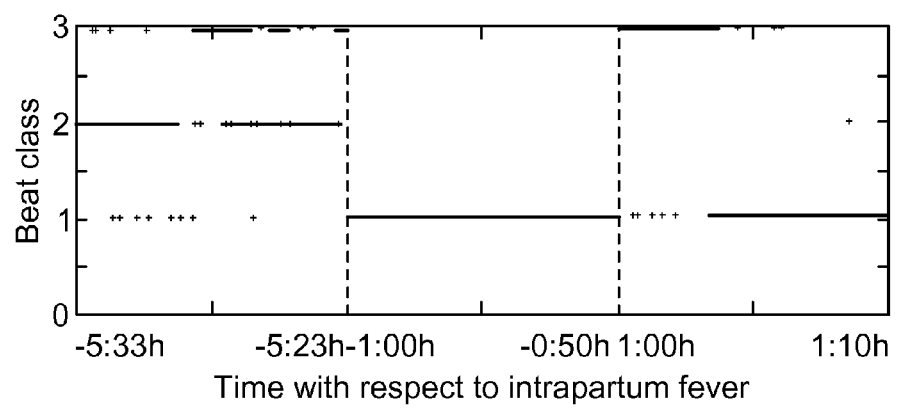
FIG. 7D shows the occurrence of different classes of ECG waveforms in one patient with respect to time.

FIGS. 7A-7C illustrate three classes of QRS complexes classified from a 7-hour dataset collected from a woman who developed chorioamnionitis during labor. FIG. 7D shows the occurrence of each beat during 10-minute intervals timed with respect to the onset of maternal fever of the same patient. Note the consistent appearance of class 1 ECG signals one hour prior to the development of fever.

Analyses of the fetal ECG waveforms also show that a measure of entropy—the degree of disorder in the similarity of the morphology of sequences the fetal heart beats—distinguishes those fetuses subject to intra-amniotic infection from those without exposure to infection.

Figure 8B:
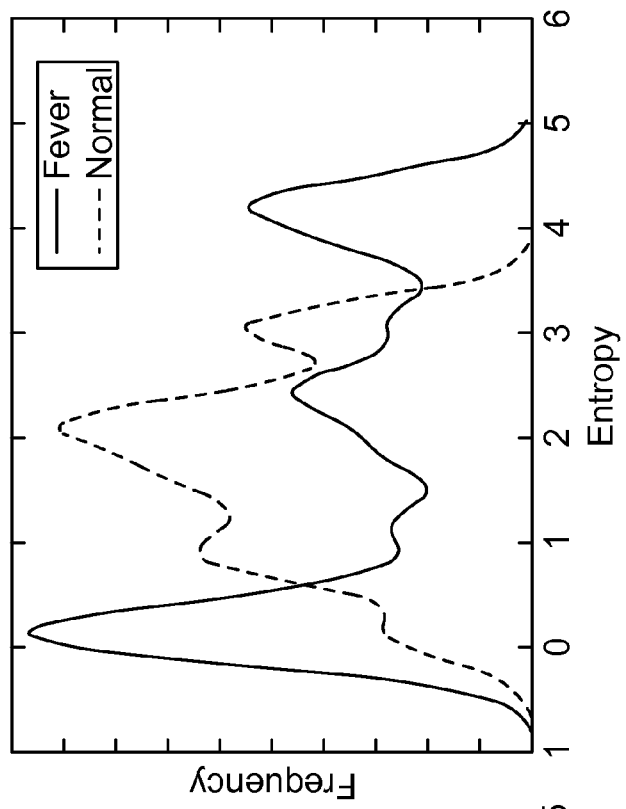
FIG. 8B illustrates the distribution of ECG entropy among fever and normal populations.
Figure 8A:
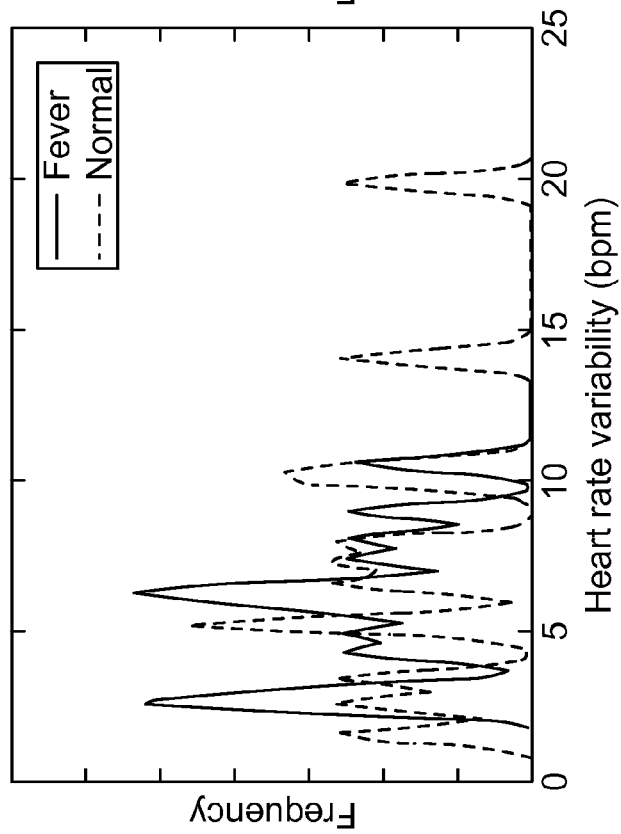
FIG. 8A illustrates the distribution of heart rate variability among fever and normal populations.

FIGS. 8A and 8B illustrate respectively the HRV analysis and entropy analysis of 30 fetal ECG datasets from women with chorioamnionitis and women without infection. As shown in FIG. 8A, the distribution of fetal HRV for fetuses subjected to chorioamnionitis (e.g., exhibiting maternal fever symptom) is not easily distinguishable from that of fetuses in an uninfected intrauterine environment. In comparison, FIG. 8B shows that, when the entropy of the fetal ECG signal is calculated for the same set of fetal ECG data, fetuses subjected to chorioamnionitis are bimodally distributed with respect to entropy, whereas fetuses in an uninfected environment are essentially normally distributed. In other words, an ECG waveform having a very low (e.g., 0) or very high (e.g., 4) entropy indicates a higher probability of developing chorioamnionitis. In some examples, the distributions of observed entropy measures in two known classes of patients (e.g., condition present versus normal) are used to form a likelihood ratio test to classify a patient based on an observed entropy.

In some examples, different patterns of electrophysiological behaviors can be correlated with medical conditions using specific biochemical markers of such conditions, e.g., markers of inflammation and brain injury measured from fetal umbilical cord collected from the patient. Umbilical cord blood interleukin-6, for example, is significantly elevated in fetuses that develop sepsis compared with fetuses that do not develop sepsis. Cord blood levels of IL-6 greater than 108.5 pg/ml are considered 95% sensitive and 100% specific for neonatal sepsis.

Figure 9:
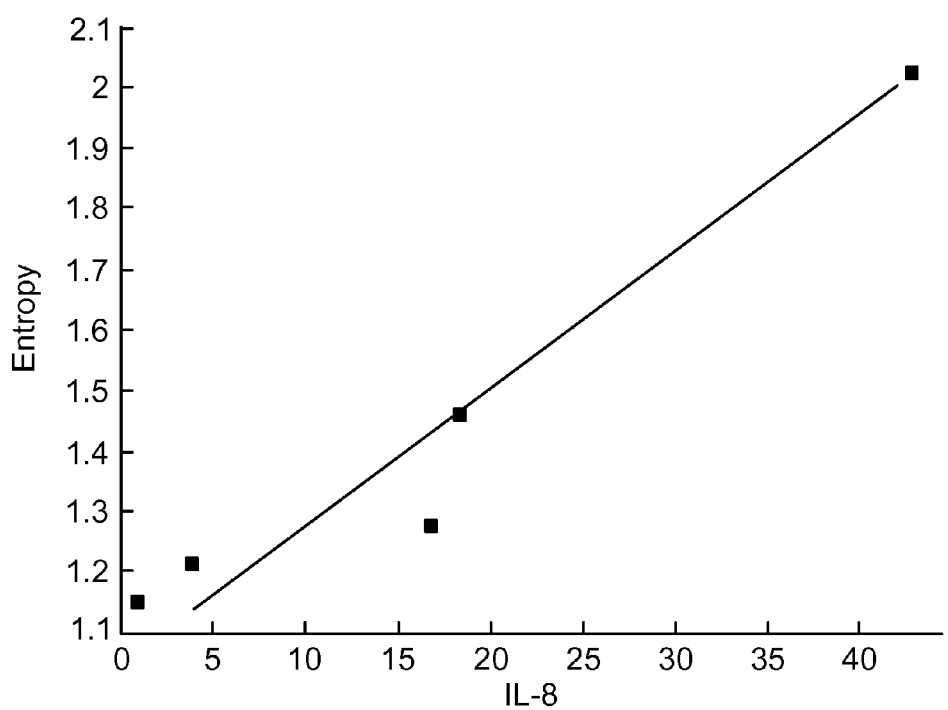
FIG. 9 illustrates a correlation between ECG entropy and IL-8 level.

FIG. 9 shows an association between the morphologic entropy of the fetal ECG and fetal umbilical cord serum interleukin-8 (IL-8) levels. Increasing levels of IL-8 are correlated (e.g., having a substantially linear relationship) with increasing disorder in the fetal ECG morphology. One possible explanation of this correlation is that an in-utero fetal inflammation/infection is associated with quantitative changes in the fetal ECG, reflecting altered electrophysiological signaling at the level of the fetal brainstem, fetal myocardium, or both.

Another related application relates to using characteristics of ECG signals to discriminate between different possible causes of medical conditions. Various causes of diseases may induce changes in ECG morphology through different mechanisms, which may in turn lead to distinguishable patterns in ECG morphologies. For example, infection, which is one explanation for inflammation, may induce a morphological change in fetal ECG signals through brain stem and myocardium level; while preeclampsia (pregnancy-induced hypertension) is likely to affect the ECG morphologies through mechanism of placental failure. The various presentations of ECG morphologies can therefore be used as a basis for discriminating between different causes of certain diseases.

In some embodiments, the feature extractor 253 performs signal analysis that is not necessarily related to ECG signals. For example, muscle signals are detected using the surface electrodes or conventional pressure sensors for contractions, and timing and intensity of uterine contractions are estimated. This approach has an advantage of providing a single monitoring device being applied to the mother, while providing multiple clinically-relevant signals.

In some embodiments, the fetal monitoring system 100 may incorporate functions of other medical diagnostic tools to enhance fetal ECG detection and/or assist clinical evaluations. For example, a maternal reference signal can be obtained using other sensing modes, such as ultrasound, imaging, and blood pressure sensing, to facilitate fetal ECG extraction. Also, histological and pathological data of a patient can be assessed in conjunction with ECG data to detect inflammation and neuronal injury before the onset of permanent disability.

It is to be understood that the foregoing description is intended to illustrate and not to limit the scope of the invention, which is defined by the scope of the appended claims. Other embodiments are within the scope of the following claims.

What is claimed is:
1. A system for monitoring fetal electrical activity, the system comprising:
a plurality of contact elements, each of the plurality of contact elements configured for attachment to an external skin surface of a pregnant female; and at least two sets of electrodes associated with each of the plurality of contact elements such that electrodes of each set contact the external skin surface of the pregnant female when the associated contact element is attached, the at least two sets of electrodes comprising a first set of electrodes arranged in a first pattern and a second set of electrodes separate from the first set of electrodes and arranged in a second pattern distinct from the first pattern, each of the plurality of contact elements having its sets of electrodes configured in a unique pattern such that at least one electrode from a first contact element and a corresponding electrode from a second contact element form a cross-body lead, fetal electrical activity being detected by the electrodes when the contact elements are attached.

2. The system of claim 1, wherein the fetal electrical activity is indicative of fetal cardiac activity, fetal brain activity, fetal body position, or a combination thereof.

3. The method of claim 1, wherein the plurality of contact elements are each configured for attachment to an external skin surface in the torso region of the pregnant female.

4. The method of claim 3, wherein the plurality of contact elements are each configured for attachment to a different area of the torso.

5. The method of claim 4, wherein the plurality of contact elements are configured for attachment to the abdominal region, the lumbar region and one or more side regions of the torso, or any combination thereof.

6. The system of claim 1 wherein each of the plurality of contact elements comprises a patch.

7. The system of claim 6 wherein the patch comprises a fabric.

8. The system of claim 6 wherein the patch includes an adhesive for adhering to the external skin surface of the pregnant female.

9. The system of claim 1 wherein the electrode pattern of each of the at least two sets of electrodes of each of the contact elements is configured in relation to an anatomical reference point of the pregnant female.

10. The system of claim 9 wherein each of the contact elements includes a reference element to guide attachment of the contact element to the external skin surface of the torso of the pregnant female.

11. The system of claim 9 wherein the anatomical reference point is the maternal heart, the belly button, the iliac arch, or the spine.

12. The system of claim 1 wherein fetal electrical activity is detected by the electrodes when the contact elements are attached regardless of the position of the fetus within the pregnant female.

13. The system of claim 1 wherein a first one of the plurality of contact elements is configured for attachment to the external skin surface of an abdominal region of the torso of the pregnant female and a second one of the plurality of contact elements is configured for attachment to the external skin surface of a lumbar region of the torso of the pregnant female.

14. The system of claim 13 wherein a third one of the plurality of contact elements is configured for attachment to the external skin surface of a right side of the torso of the pregnant female and a fourth one of the plurality of contact elements is configured for attachment to the external skin surface of a left side of the torso of the pregnant female.

15. The system of claim 1 wherein each of the electrode patterns comprises at least two dry electrodes.

16. The system of claim 1 wherein each of the electrode patterns comprises at least two gel-adhesive electrodes.

17. The system of claim 1 wherein each of the electrode patterns comprises at least one dry electrode and at least one gel-adhesive electrode.

18. The system of claim 1, wherein the plurality of contact elements comprise a minimum of 6 electrodes combined between the plurality of contact elements.

19. The system of claim 1, wherein the plurality of contact elements comprises a maximum of 64 electrodes combined between the plurality of contact elements.

20. The system of claim 1, wherein the plurality of contact elements comprise 32 electrodes between the plurality of contact elements.

21. The system of claim 1, wherein each of the at least two sets of electrodes associated with each of the plurality of contact elements is configured in a predetermined pattern.

22. The system of claim 1, wherein one or more of the plurality of contact elements further comprises an electronic identification tag.

23. The system of claim 1, wherein one or more of the plurality of contact elements is configured for long range, wireless transmission of fetal electrical activity.

24. The system of claim 1, wherein the system is configured for a single-use.

25. A system for monitoring fetal electrical activity, the system comprising:
a plurality of contact elements, each of the plurality of contact elements configured for attachment to different areas on the external skin surface of a pregnant female; and
at least two sets of electrodes associated with each of the plurality of contact elements such that electrodes of each set contact the different external skin surface areas of the pregnant female when the associated contact element is attached, the at least two sets of electrodes comprising a first set of electrodes arranged in a first pattern and a second set of electrodes separate from the first set of electrodes and arranged in a second pattern distinct from the first pattern, and at least one electrode from a first contact element and a corresponding electrode from a second contact element form a cross-body lead, fetal electrical activity being detected by the electrodes when the contact elements are attached.

26. The system of claim 25, wherein the fetal electrical activity is indicative of fetal cardiac activity, fetal brain activity, fetal body position, or a combination thereof.

27. The method of claim 25, wherein the plurality of contact elements are each configured for attachment to a different external skin surface areas in the torso region of the pregnant female.

28. The method of claim 27, wherein the plurality of contact elements are configured for attachment to the abdominal region, the lumbar region and one or more side regions of the torso, or any combination thereof.

29. The system of claim 25 wherein each of the plurality of contact elements comprises a patch.

30. The system of claim 29 wherein the patch comprises a fabric.

31. The system of claim 30 wherein the patch includes an adhesive for adhering to the external skin surface of the pregnant female.

32. The system of claim 25 wherein the electrode pattern of each of the contact elements is configured in a unique pattern.

33. The system of claim 25, wherein the electrode pattern of each of the at least two sets of electrodes of each of the contact elements is configured in relation to an anatomical reference point of the pregnant female.

34. The system of claim 33 wherein one or more of the contact elements includes a reference element to guide attachment of the contact element to the particular external skin surface area of the torso of the pregnant female.

35. The system of claim 33 wherein the anatomical reference point is the maternal heart, the belly button, the iliac arch, or the spine.

36. The system of claim 25 wherein fetal electrical activity is detected by the electrodes when the contact elements are attached regardless of the position of the fetus within the pregnant female.

37. The system of claim 25 wherein a first one of the plurality of contact elements is configured for attachment to the external skin surface of an abdominal region of the torso of the pregnant female and a second one of the plurality of contact elements is configured for attachment to the external skin surface of a lumbar region of the torso of the pregnant female.

38. The system of claim 37 wherein a third one of the plurality of contact elements is configured for attachment to the external skin surface of a right side of the torso of the pregnant female and a fourth one of the plurality of contact elements is configured for attachment to the external skin surface of a left side of the torso of the pregnant female.

39. The system of claim 25 wherein each of the electrode patterns comprises at least two dry electrodes.

40. The system of claim 25 wherein each of the electrode patterns comprises at least two gel-adhesive electrodes.

41. The system of claim 25 wherein each of the electrode patterns comprises at least one dry electrode and at least one gel-adhesive electrode.

42. The system of claim 25, wherein the plurality of contact elements comprise a minimum of 6 electrodes combined between the plurality of contact elements.

43. The system of claim 25, wherein the plurality of contact elements comprises a maximum of 64 electrodes combined between the plurality of contact elements.

44. The system of claim 25, wherein the plurality of contact elements comprise 32 electrodes between the plurality of contact elements.

45. The system of claim 25, wherein each of the at least two sets of electrodes associated with each of the plurality of contact elements is configured in a predetermined pattern.

46. The system of claim 25, wherein one or more of the plurality of contact elements further comprises an electronic identification tag.

47. The system of claim 25, wherein one or more of the plurality of contact elements is configured for long range, wireless transmission of fetal electrical activity.

48. The system of claim 25, wherein the system is configured for a single-use.

* * * * *